United States Patent
Draper et al.

(10) Patent No.: US 9,662,314 B2
(45) Date of Patent: May 30, 2017

(54) COMPOUNDS AND METHODS FOR THE TREATMENT OF MUSCULAR DISEASE, AND RELATED SCREENING METHODS

(71) Applicants: Tufts Medical Center, Inc., Boston, MA (US); Children's Medical Center Corporation, Boston, MA (US)

(72) Inventors: Isabelle Draper, Andover, MA (US); Louis M. Kunkel, Westwood, MA (US); Matthew S. Alexander, Boston, MA (US); Alan S. Kopin, Wellesley, MA (US)

(73) Assignees: Tufts Medical Center, Inc., Boston, MA (US); Children's Medical Center Corporation, Boston, MA (US)

(*) Notice: Subject to any disclaimer, the term of this patent is extended or adjusted under 35 U.S.C. 154(b) by 454 days.

(21) Appl. No.: 14/352,717

(22) PCT Filed: Oct. 19, 2012

(86) PCT No.: PCT/US2012/061041
§ 371 (c)(1),
(2) Date: Apr. 18, 2014

(87) PCT Pub. No.: WO2013/059606
PCT Pub. Date: Apr. 25, 2013

(65) Prior Publication Data
US 2014/0243378 A1    Aug. 28, 2014

Related U.S. Application Data

(60) Provisional application No. 61/549,940, filed on Oct. 21, 2011.

(51) Int. Cl.
| | | |
|---|---|---|
| *A61K 31/335* | (2006.01) |
| *A61K 31/075* | (2006.01) |
| *A61K 31/44* | (2006.01) |
| *A61K 31/11* | (2006.01) |
| *A61K 31/122* | (2006.01) |
| *A61K 31/192* | (2006.01) |
| *A61K 31/216* | (2006.01) |
| *A61K 31/357* | (2006.01) |
| *A61K 31/4402* | (2006.01) |
| *A61K 31/4406* | (2006.01) |
| *A61K 31/4409* | (2006.01) |
| *A61K 31/455* | (2006.01) |
| *A61K 31/7105* | (2006.01) |
| *C12N 15/113* | (2010.01) |

(52) U.S. Cl.
CPC ............. *A61K 31/44* (2013.01); *A61K 31/11* (2013.01); *A61K 31/122* (2013.01); *A61K 31/192* (2013.01); *A61K 31/216* (2013.01); *A61K 31/357* (2013.01); *A61K 31/4402* (2013.01); *A61K 31/4406* (2013.01); *A61K 31/4409* (2013.01); *A61K 31/455* (2013.01); *A61K 31/7105* (2013.01); *C12N 15/113* (2013.01)

(58) Field of Classification Search
CPC ............................ C07D 319/06; A61K 31/085
USPC ............................................ 514/452, 717, 718
See application file for complete search history.

(56) References Cited

U.S. PATENT DOCUMENTS

| 4,500,544 A | 2/1985 | Hosokawa et al. |
| 4,542,143 A | 9/1985 | Hosokawa et al. |
| 6,605,639 B1 | 8/2003 | Tamura et al. |
| 2005/0153918 A1 | 7/2005 | Chabot et al. |
| 2007/0054259 A1 | 3/2007 | Kim et al. |
| 2010/0136568 A1 | 6/2010 | Rigby |
| 2010/0317840 A1 | 12/2010 | Chen et al. |

FOREIGN PATENT DOCUMENTS

| WO | WO-92/02137 A1 | 2/1992 |
| WO | WO-2011/026200 | 3/2011 |
| WO | WO-2011/109823 | 9/2011 |

OTHER PUBLICATIONS

Draper et al., "The evoluntionarily conserved RNA binding protein Smooth is essential for maintaining normal muscle function," Fly, 3(4):235-246 (2009).
International Search Report dated Mar. 4, 2013 from PCT/US2012/061041.
Alexander et al., "Regulation of DMD pathology by an ankyrin-encoded miRNA," Skeletal Muscle, 1:27 (2011).

*Primary Examiner* — Raymond Henley, III
(74) *Attorney, Agent, or Firm* — Dana M. Gordon; Foley Hoag LLP

(57) ABSTRACT

Disclosed are methods of treating a muscle disease and improving normal muscle function by administering a therapeutically effective amount of an isoprenoid antibiotic. Also disclosed are methods of upregulating hnRNP L and hnRNP L targets by administering a therapeutically effective amount of an isoprenoid antibiotic. Methods of screening compounds for use in treating muscle disease and improving muscle function are also described.

20 Claims, 8 Drawing Sheets

The control gene for the qPCR analyses is β-actin; corresponding primers are available.

Primer pair 1/Exon 6        Primer pair 2/Exon 10        Beta actin

Exon 6 efficiency = 94%    Exon 10 efficiency = 109%    Beta actin efficiency = 116%

Figure 5

|  | 48hrs : 30% confluent Infect | Day 0 Diff: 90% confluent Started Differentiation (2% FBS) | Day 2 Diff | Day 4 Diff |
|---|---|---|---|---|
| shLuc (cont) | | | | |
| shHNRNP L | | | | |
| | no change | no change | no change | marked change |

Figure 6

|  | Day 7 Diff | Day 10 Diff | Day 14 Diff |
|---|---|---|---|
| shLuc (-cont) | | | |
| shHNRNP L | | | |

Figure 11

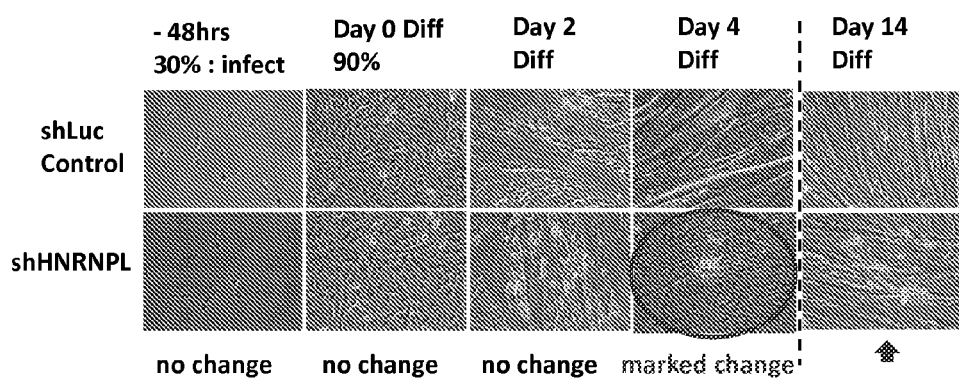

Figure 12

| Library name | Description | # of drugs | Screen period |
|---|---|---|---|
| MPRC small molecules | 22 primary libraries and diversity collections (100-200 compounds each). Unique structures that do not overlap in chemical space with molecules currently in the PubChem database. | ~ 3K | Year 1 |
| MPRC natural products | Extracts from plants used in traditional Chinese medicine. Unique molecules with unusual/ unexplored structures. | 3.7K | Year 1 |
| CB/NT Broad Outreach Laboratory collection | FDA-approved bioactive drugs. | 1.6K | Year 2 |

Figure 13

```
CLUSTAL W (1.83) multiple sequence alignment _Homo sapiens hnRNPL isoform
a vs. isoform b hnRNPL_isoform_a_NP_001524.2
MSRRLLPRAEKRRRRLEQRQQPDEQRRRSGAMVKMAAAGGGGGGGRYYGG
hnRNPL_isoform_b_NP_001005335.1    --------------------------------------
---------- hnRNPL_isoform_a_NP_001524.2
GSEGGRAPKRLKTDNAGDQHGGGGGGGGGAGAAGGGGGGENYDDPHKTPA
hnRNPL_isoform_b_NP_001005335.1    --------------------------------------
---------- hnRNPL_isoform_a_NP_001524.2
SPVVHIRGLIDGVVEADLVEALQEFGPISYVVVMPKKRQALVEFEDVLGA
hnRNPL_isoform_b_NP_001005335.1    -------------------------------
MPKKRQALVEFEDVLGA

* * * * * * * * * * * * * * * * * hnRNPL_isoform_a_NP_001524.2
CNAVNYAADNQIYIAGHPAFVNYSTSQKISRPGDSDDSRSVNSVLLFTIL
hnRNPL_isoform_b_NP_001005335.1
CNAVNYAADNQIYIAGHPAFVNYSTSQKISRPGDSDDSRSVNSVLLFTIL

*************************************************** hnRNPL_isoform_a_NP_001524.2
NPIYSITTDVLYTICNPCGPVQRIVIFRKNGVQAMVEFDSVQSAQRAKAS
hnRNPL_isoform_b_NP_001005335.1
NPIYSITTDVLYTICNPCGPVQRIVIFRKNGVQAMVEFDSVQSAQRAKAS

*************************************************** hnRNPL_isoform_a_NP_001524.2
LNGADIYSGCCTLKIEYAKPTRLNVFKNDQDTWDYTNPNLSGQGDPGSNP
hnRNPL_isoform_b_NP_001005335.1
LNGADIYSGCCTLKIEYAKPTRLNVFKNDQDTWDYTNPNLSGQGDPGSNP

*************************************************** hnRNPL_isoform_a_NP_001524.2
NKRQRQPPLLGDHPAEYGGPHGGYHSHYHDEGYGPPPPHYEGRRMGPPVG
hnRNPL_isoform_b_NP_001005335.1
NKRQRQPPLLGDHPAEYGGPHGGYHSHYHDEGYGPPPPHYEGRRMGPPVG

*************************************************** hnRNPL_isoform_a_NP_001524.2
GHRRGPSRYGPQYGHPPPPPPPPEYGPHADSPVLMVYGLDQSKMNCDRVF
hnRNPL_isoform_b_NP_001005335.1
GHRRGPSRYGPQYGHPPPPPPPPEYGPHADSPVLMVYGLDQSKMNCDRVF

```
hnRNPL_isoform_a_NP_001524.2
NVFCLYGNVEKVKFMKSKPGAAMVEMADGYAVDRAITHLNNNFMFGQKLN
hnRNPL_isoform_b_NP_001005335.1
NVFCLYGNVEKVKFMKSKPGAAMVEMADGYAVDRAITHLNNNFMFGQKLN

************************************************** hnRNPL_isoform_a_NP_001524.2
VCVSKQPAIMPGQSYGLEDGSCSYKDFSESRNNRFSTPEQAAKNRIQHPS
hnRNPL_isoform_b_NP_001005335.1
VCVSKQPAIMPGQSYGLEDGSCSYKDFSESRNNRFSTPEQAAKNRIQHPS

************************************************** hnRNPL_isoform_a_NP_001524.2
NVLHFFNAPLEVTEENFFEICDELGVKRPSSVKVFSGKSERSSSGLLEWE
hnRNPL_isoform_b_NP_001005335.1
NVLHFFNAPLEVTEENFFEICDELGVKRPSSVKVFSGKSERSSSGLLEWE

************************************************** hnRNPL_isoform_a_NP_001524.2        SKSDALETLGFLNHYQMKNPNGPYPYTLKLCFSTAQHAS
hnRNPL_isoform_b_NP_001005335.1     SKSDALETLGFLNHYQMKNPNGPYPYTLKLCFSTAQHAS
                                    ***************************************
```

COMPOUNDS AND METHODS FOR THE TREATMENT OF MUSCULAR DISEASE, AND RELATED SCREENING METHODS

RELATED APPLICATIONS

This application is the National Stage application of PCT/US12/061041, filed Oct. 19, 2012, which claims the benefit of priority to U.S. Provisional Patent Application Ser. No. 61/549,940, filed Oct. 21, 2011, the contents of both applications are hereby incorporated by reference.

GOVERNMENT SUPPORT

This invention was made with government support under Grant No. P50 NS040828-08 awarded by the National Institutes of Health. The government has certain rights in this invention.

BACKGROUND OF THE INVENTION

Muscle diseases include many diseases and ailments that either directly, via intrinsic muscle pathology, or indirectly, via nerve or neuromuscular junction pathology, impair the functioning of the muscles. Muscular dystrophy (MD) is a group of muscle diseases that weaken the musculoskeletal system and hamper locomotion. Muscular dystrophies are characterized by progressive skeletal muscle weakness, defects in muscle proteins, and the death of muscle cells and tissue.

Myotonic Dystrophy (DM) is the most prevalent muscular dystrophy in adults, affecting 1/8000 individuals worldwide, and is incurable. There are multiple clinical manifestations of the disease including disabling musculoskeletal symptoms (myotonia, muscle weakness and wasting), ophthalmologic defects (cataract) and cognitive deficits. The genetic abnormality underlying the predominant form, DM1, is caused by a pathological expansion of CTG repeats in the 3' untranslated region of the DMPK (DM protein Kinase) gene. When transcribed, the expanded CUG entraps trans-acting RNA binding proteins (RBPs) in the cell nucleus, leading to aberrant processing of many downstream RNA targets. The prevailing model mainly focuses on MBNL1 (muscleblind like protein), a splicing factor which is sequestered on the toxic CUG repeats. Mounting evidence from the literature indicates that other factors co-regulate MBNL 1-dependent RNA processing, and thus play a key role in the pathogenesis of DM1.

DM1 is a dominantly inherited neuromuscular disease characterized by progressive myopathy and myotonia, due to large expansions (>50 and up to 4000) of CTG-repeats in the 3' UTR of the DMPK gene. The disease also results in a combination of heart defects, cataract, GI dysfunction, insulin resistance and cognitive deficits, and is thus complex and generalized. The transcribed CUG-expanded RNAs adopt an abnormal hairpin structure and accumulate in the nucleus as foci, where they entrap, or more indirectly deregulate, RNA processing proteins (RBPs). It is well-established that DM1 is in part caused by the dysfunction of two well-characterized RBPs, MBNL1 and CUGBP1 (CUG binding protein 1, aka CELF1), resulting in a global misregulation of splicing events (i.e. 'spliceopathy'). Aberrant splicing in DM1 leads to the generation of isoforms that are normally found in a different developmental stage (e.g. fetal isoform produced in adult muscle), or in a different tissue (e.g. non-muscle isoform in muscle), and are not functional in the temporal/local cellular context. In addition to misssplicing, abnormal translation, subcellular localization and turn-over of RNA targets have been reported in DM1. Studies of corresponding DM1 mouse models have greatly enhanced understanding of the mechanism of the pathologic cascade that underlies the disease. Despite these major advances, it has become increasingly apparent that MBNL1/CUGPB1 functional imbalance does not fully explain DM1 pathophysiology. For example, in MBNL1-deficient mice muscle wasting (as observed in DM1 patients) is not recapitulated, nor is the full spectrum of aberrantly spliced exons that is associated with DM1 in humans. A 2-fold elevation of CUGBP1 levels in transgenic mice (comparable to that observed in DM1 muscle) does not induce changes in alternative splicing. Given that RBPs often act in protein complexes, these observations prompted an active search for additional factors that likely contribute to the disease. Among the candidates, hnRNP H, and more recently Staufen1 have been shown to modulate the MBNL1/CUGBP1-dependent aberrant splicing in DM, but other factors have yet to be uncovered.

Isoprenoid antibiotics were originally isolated from the phytopathogenic fungus Ascochyta viciae. (Sasaki, H. et al., Isolation and structure of ascofuranone and ascofranol, antibiotics with hypolipidemic activity. *J Antibiot (Tokyo)*, 1973, 26:676-680). Among them, ascochlorin and ascofuranone have been shown to be non-toxic compounds. Structurally related compounds have been subsequently isolated from other fungi (e.g., *Fusarium, Cylindrocladium, Cylindrocladium ilicicola, Nectria coccinea, Colletotrichum nicotianae, Acremonium luzulae, Cephalosporium diospyri, Verticillium, Cylindrocarpon lucidum, Nigrosabulum globosum*, and the insect pathogenic fungus *Verticillium hemipterigenum*). (Hosono, K. et al., Ll-z1272 alpha epoxide, a precursor of ascochlorin produced by a mutant of ascochyta viciae, *J Antibiot (Tokyo)*, 2009, 62:571-574; Seephonkai, P. et al., A novel ascochlorin glycoside from the insect pathogenic fungus *verticillium hemipterigenum* bcc 2370, *J Antibiot (Tokyo)*, 2004, 57:10-16).

Ascochlorin and ascofuranone display antitumorigenic properties, both in vitro and in vivo. (Jeong J H, et al. *J Cell Biochem*. 2012 April; 113(4):1302-13; Kang, J. H. et al. *J Biol Chem*. 2012 May 4; 287(19):15661-71; Jeong, J. H. and Chang, Y. C., Ascochlorin, an isoprenoid antibiotic, induces g1 arrest via downregulation of c-myc in a p53-independent manner, *Biochem Biophys Res Commun.*, 2010, 398:68-73; Magae, J. et al., Antitumor and antimetastatic activity of an antibiotic, ascofuranone, and activation of phagocytes, *J Antibiot (Tokyo)*, 1988, 41:959-965; Nakajima, H. et al., Aberrant expression of fra-1 in estrogen receptor-negative breast cancers and suppression of their propagation in vivo by ascochlorin, an antibiotic that inhibits cellular activator protein-1 activity. *J Antibiot (Tokyo)*, 2007, 60:682-689). In a murine model of mammary carcinoma, it was demonstrated that intraperitoneal administration of ascochlorin significantly suppressed cancer growth and prolonged survival. (Nakajima et al., 2007).

In addition to anticancer properties, ascochlorin and its derivatives exhibit a wide range of physiological activities, including antimicrobial/antiviral activity, trypanocidal properties, hypolipidemic activity, suppression of hypertension, improvement of type I and II diabetes, and immunomodulation. (Yabu, Y. et al., The efficacy of ascofuranone in a consecutive treatment on *trypanosoma brucei brucei* in mice, *Parasitol Int*. 2003, 52:155-164; Hosono et al., 2009).

There exists a need for non-toxic compounds for the treatment of muscle diseases.

SUMMARY OF THE INVENTION

One aspect of the invention relates to a method of treating a muscle disease, comprising the step of administering to a mammal in need thereof a therapeutically effective amount of an isoprenoid antibiotic.

Another aspect of the invention relates to a method of improving normal muscle function, comprising the step of administering to a mammal in need thereof a therapeutically effective amount of an isoprenoid antibiotic.

Yet another aspect of the invention relates to a method of upregulating hnRNP L, comprising the step of administering to a mammal in need thereof a therapeutically effective amount of an isoprenoid antibiotic.

Another aspect of the invention relates to a method of upregulating a hnRNP L target, comprising the step of administering to a mammal in need thereof a therapeutically effective amount of an isoprenoid antibiotic.

In certain embodiments, the invention relates to a RNA interference (RNAi) agent capable of reducing, attenuating, or abolishing the production of hnRNP L in a cell, wherein the cell is a mammalian myoblast or a mammalian myotube.

In certain embodiments, the invention relates to a method of attenuating hnRNP L gene expression in a cell, comprising the steps of:
  contacting a plurality of cells with a recombinant nucleic acid construct or vector, wherein the recombinant nucleic acid construct or vector encodes any one of the aforementioned RNAi agents, and wherein the cells are mammalian myoblasts, thereby producing a subset of cells that express the RNAi in an amount sufficient to attenuate hnRNP L gene expression in the subset of cells.

In certain embodiments, the invention relates to a method comprising the steps of:
  contacting a plurality of cells with a recombinant nucleic acid construct or vector, wherein the recombinant nucleic acid construct or vector encodes any one of the aforementioned RNAi agents, and wherein the cells are mammalian myoblasts, thereby producing a subset of cells that express the RNAi in an amount sufficient to attenuate hnRNP L gene expression in the subset of cells;
  selecting the subset of cells, thereby forming a selected subset of cells;
  exposing the selected subset of cells to a compound; and
  analyzing the progression of differentiation of the mammalian myoblasts into mammalian myotubes.

BRIEF DESCRIPTION OF THE DRAWINGS

FIG. 5 depicts images showing that shRNAi knockdown of hnRNP L in differentiating human myoblasts results in death of the myotubes at Day 4 Differentiation (circle). shLuc: control anti-luciferase; shHNRP L: anti-hnRNP L.

FIG. 6 depicts images showing that shRNAi knockdown of HNRNP L in differentiating human myoblasts results in disorganized myotubes at Day 14 Differentiation (arrow). ShLuc: anti-luciferase control virus; shHNRP L: anti-hnRNP L virus.

FIG. 11 depicts the effect of shRNAi knockdown (KD) of hnRNP L in differentiating human myoblasts. HnRNP L KD results in the death of multi-nucleated myotubes at Day 4 Differentiation (circle). HnRNP L KD results in disorganized myotubes at Day 14 Differentiation (arrow). shLuc: anti-luciferase control virus; shHNRNP L: anti-hnRNP L virus.

FIG. 12 tabulates the chemical libraries that will be screened using the hnRNP L-deficient myoblast HTS assay.

FIG. 13 depicts a sequence alignment of hnRNPL a and b sequences

DETAILED DESCRIPTION OF THE INVENTION

Overview

Figure 1:
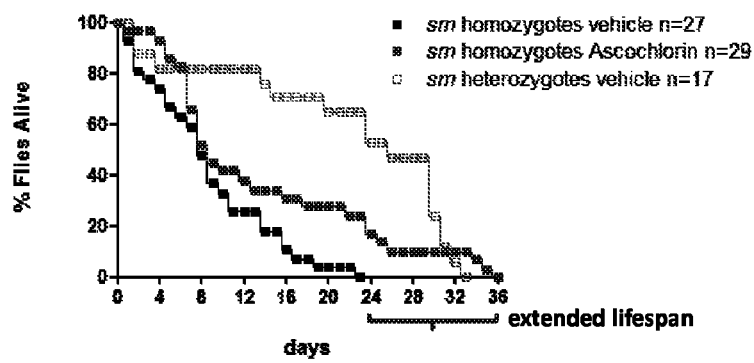
FIG. 1 shows adult smooth mutant *Drosophila* flies treated with ascochlorin display prolonged survival time. Smooth mutant *Drosophila* flies (sm homozygotes, that develop muscle dystrophy) were maintained on paper discs soaked either with ascochlorin (Santa Cruz Biotechnology, 1 mM solution in 9% sucrose, 10% ethanol), or with vehicle alone. The treatment was maintained throughout the lifespan of the organism. Unaffected control siblings (sm heterozygotes) were maintained on vehicle. The number of dead flies was recorded daily, and percent survival was plotted as a function of time in days.

The RBP hnRNP L (heteronuclear ribonucleoprotein L) may play a role in the pathogenesis of DM1, implying that its therapeutic modulation holds promise in the treatment of DM. Downregulation of the fly homolog of hnRNP L, smooth, leads to pronounced muscle degeneration and premature death, in adult flies. In addition, hnRNP L binds to MBNL1 in vitro (in HEK293 cells) hnRNP L (i) is essential for myofiber survival in vitro, (ii) is differentially expressed in DM1 muscle cell line and (iii) regulates the splicing of exons that are aberrantly processed in DM1.

In certain embodiments, the invention relates to the decrease in hnRNP L activity in DM1 muscle, due to its interaction with sequestered MBNL 1. In certain embodiments, the invention relates to a method of increasing hnRNP L levels in a cell comprising contacting the cell with a therapeutically effective amount of a compound.

The splicing factor hnRNP L may be a candidate modifier of myotonic dystrophy/MBNL1 function. In certain embodiments, the invention relates to investigations designed to further establish the relevance of this protein in the pathogenic mechanisms underlying DM1. In certain embodiments, the invention relates to the investigation of the spectrum of alternative exons regulated by hnRNP L in human muscle cells, and the definition of the overlap with exons that are aberrantly spliced in DM1 (as identified in previous transcriptome analyses of muscle isolated from DM1 patients). Knowledge of the pathogenic mechanisms that are regulated by hnRNP L in DM can be translated into the identification of drugs that target these processes. Despite major efforts that have focused on myotonic dystrophy, only symptomatic therapies are currently available. In certain embodiments, the invention relates to a cell-based high throughput screen that is designed to enable the identification of compounds that not only lead to symptomatic relief, but can enhance the survival of mature myofibers that would otherwise degenerate.

In certain embodiments, the invention relates to a cell-based assay that uniquely assesses the survival of multi-nucleated human myofibers, where alternative splicing is de-regulated. Using the cell-based assay, pharmacological compounds that improve myotube survival/maintenance can be identified. Hit compounds may provide novel chemical entities for the development of DM1 therapeutics. Using the cell-based assay, the spectrum of RNA targets that are regulated by hnRNP L in muscle can be defined. A better understanding of hnRNP L-dependent pathways in muscle will provide novel means to fight spliceopathy-induced muscle disease (e.g. DM1).

Link to the Splicing Factor hnRNP L/Downstream RNA Targets

Proteome analysis has demonstrated that ascochlorin treatment of human osteosarcoma cells (U2OS) results in a ≥10 fold increase in the levels of three proteins, including the splicing factor hnRNP L (most up-regulated protein, 12×), as well as BIN1 (third most up-regulated protein, 10×). (Kang, J. H. et al., Proteome analysis of responses to ascochlorin in a human osteosarcoma cell line by 2-d gel electrophoresis and maldi-tof MS, *J Proteome Res.*, 2006, 5:2620-2631). We have determined by bioinformatics analysis that BIN1 is a candidate target of hnRNP L (Table 1, below). Importantly, mutations in BIN1 (alternative name, amphiphysin 2) are linked to centronuclear myopathies in humans. (Toussaint, A. et al., Defects in amphiphysin 2 (BIN1) and triads in several forms of centronuclear myopathies, *Acta Neuropathol.*, 2011, 121:253-266).

Recent studies also demonstrated that the methylated derivative of ascochlorin, 4-O-methylascochlorin (MAC), increases the expression of vascular endothelial growth factor (VEGF) and glucose transporter 1 (GLUT-1). (Jeong, J. H. et al., 4-o-methylascochlorin, methylated derivative of ascochlorin, stabilizes HIF-1-alpha via AMPK activation, *Biochem. Biophys. Res. Commun.*, 2011, 406:353-358). Both VEGF and GLUT-1 RNAs are well-established targets of hnRNP L. (Hamilton, B. J. et al., HnRNP a2 and hnRNP 1 bind the 3'utr of glucose transporter 1 mRNA and exist as a complex in vivo, *Biochem. Biophys. Res. Commun.*, 1999, 261:646-651; Ray, P. S. et al., A stress-responsive RNA switch regulates VEGFa expression, *Nature,* 2009, 457:915-919; Shih, S. C. and Claffey, K. P., Regulation of human vascular endothelial growth factor mRNA stability in hypoxia by heterogeneous nuclear ribonucleoprotein 1, *J. Biol. Chem.*, 1999, 274:1359-1365).

Previous reports in the literature have demonstrated that hnRNP L is a key regulator of alternative splicing that can promote either the inclusion, or the exclusion, of tissue specific exons. Interestingly, hnRNP L binding motifs were shown to be enriched in alternative splicing events that are associated with myogenic differentiation. We recently carried out a bioinformatic analysis of a compendium of known human alternative splicing events to identify sequences that include the hnRNP L binding motif, and are expressed in skeletal muscle and/or the heart. This analysis revealed 46 conserved putative targets of hnRNP L in muscle and the heart. Importantly, the list includes nine targets, APP, BIN1, DMD, DTNA, MAPT, MEF2A, PPP2R5C, SORBS1 and TTN, which are known to be aberrantly spliced in DM1 patients. This is a remarkably high number, given that to date, a total of less than 30 splicing defects have been confirmed in DM1 patients.

TABLE 1

Candidate RNA targets of hnRNP L/SMOOTH in skeletal muscle and/or the heart.

| Human Gene | Description | Associated Muscle/Heart Disease in Humans | Drosophila Homolog |
|---|---|---|---|
| ABl1 | ABL interactor 1/spectrin SH3 | | Abi |
| ACSS2 | Acetyl Coenzyme A synthetase | | AcCoAS |
| AGAP3 | ArfGAP GTPase ankyrin repeat and PH domain containing | | cenG1A |
| AGXT2L2 | Alanine glyoxylate aminotransferase 2 | | CG8745 |
| APP | Beta amyloid precursor | | Appl |
| ATP2B1 | Plasma membrane calcium ATPase | | PMCA |
| ATP2B4 | Plasma membrane calcium ATPase | | PMCA |
| BIN1 | Bridging integrator | Centronuclear myopathy | Amph |
| BPTF | Nucleosome remodeling factor subunit | | E(bx) |
| C12orf41 | UNKNOWN | | dgt1 |
| C14orf133 | UNKNOWN | | Vps16B |

TABLE 1-continued

Candidate RNA targets of hnRNP L/SMOOTH in skeletal muscle and/or the heart.

| Human Gene | Description | Associated Muscle/Heart Disease in Humans | Drosophila Homolog |
|---|---|---|---|
| DMD | Dystrophin | Duchenne/Becker muscular dystrophy, Dilated cardiomyopathy | Dys |
| DTNA | Dystrobrevin | | Dyb |
| ElF2C2 | Argonaute translation factor 2C | | AGO1 |
| EPB41L2 | UNKNOWN | | cora |
| FMNL2 | Formin | | CG32138 |
| GARNL1 | Ral GTPase activating protein α subunit | | CG5521 |
| ITSN2 | Intersectin | | Dap160 |
| KIAA1217 | Homolog of murine Sickle tail | | CG32809 |
| LRRFIP1 | Leucine rich repeat flightless interacting | | CG8578 |
| MAPT | Microtubule associated Tau | | Tau |
| MAX | MYC associated factor X | | Max |
| MEF2A | Myocyte specific enhancer factor | | Mef2 |
| NCAM1 | Neural cell adhesion molecule 1 | | Fas2 |
| PALLD | Palladin | | zormin |
| PDLIM7 | PDZ and LIM domain | | Zasp52 |
| PPP2R5C | Serine/Threonine Phosphatase 2A regulatory subunit B56 | | PP2A-B' |
| PTPN3 | Tyrosine phosphatase non receptor | | Ptpmeg |
| RPGR | Retinitis pigmentosa GTPase regulator | | ca |
| RRN3 | RNA polymerase 1 specific transcription factor | | Tif-IA |
| SAD1 | Serine threonine kinase SAD | | CG6114 |
| SAMD4A | Smaug homolog 1 | | Smg |
| SEMA6D | Semaphorin 6D | | Sema-1a Sema-1b |
| SLC25A3 | Phosphate carrier protein, mitochondrial | Mitochondrial phosphate carrier deficiency (muscular hypotonia/hypertrophic cardiomyopathy) | CG9090 |
| SLC39A9 | UNKNOWN may act as a zinc transporter (by similarity) | | CG2177 |
| SMTN | Smoothelin | | Actn3 |
| SORBS1 | Sorbin and SH3 domain containing 1 | | CAP |
| STXBP5 | Tomosyn | | tomosyn |
| SVIL | Archvillin; Supervilin, | | CG33232 |
| TPM1 | Tropomyosin | Hypertrophic cardiomyopathy, Dilated cardiomyopathy | Tm1 Tm2 |
| TPM3 | Tropomyosin | Nemaline myopathy 1, Congenital cap myopathy | Tm1 Tm2 |
| TRIM66 | Tripartite motif containing 66 | | bon |
| TTN | Titin | Autosomal dominant myopathy with fatal cardiomyopathy Hypertrophic cardiomyopathy, Dilated cardiomyopathy, | bt |
| VPS29 | Vacuolar protein sorting 29 | | CG4764 |
| XPNPEP1 | Aminoacyl proline aminopeptidase | | ApepP |
| ZMYND8 | Protein kinase C binding protein 1 | | CG1815 |

Compounds

TABLE 2

Formula 1

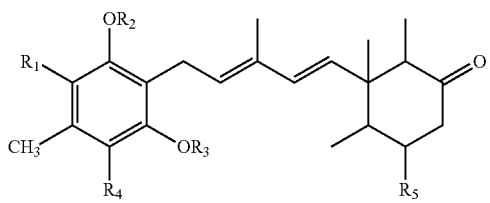

| Compound # | $R_1$ | $R_2$ | $R_3$ | $R_4$ | $R_5$ |
|---|---|---|---|---|---|
| 1 | CHO | H | H | Cl | H |
| 2 | CHO | H | H | Cl | OAc |
| 3 | CHO | H | H | Br | H |
| 4 | CHO | H | H | H | H |

TABLE 2-continued

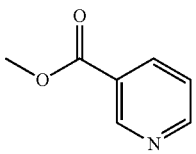

Formula 1

| Compound # | R₁ | R₂ | R₃ | R₄ | R₅ |
|---|---|---|---|---|---|
| 5 | CHO | H | CH₃CO | Cl | H |
| 6 | CHO | H | CH₃ | Cl | H |
| 7 | CHO | CH₃ | CH₃ | Cl | H |
| 8 | CHO | CH₃CO | CH₃ | Cl | H |
| 9 | CHO | CH₃ | CH₃CO | Cl | H |
| 10 | CHO | CH₃ | H | Cl | H |
| 11 | CHO | H | CH₃CH₂ | Cl | H |
| 12 | CHO | H | Allyl | Cl | H |
| 13 | CHO | H | Butyl | Cl | H |
| 14 | CHO | H | CH₂COOH | Cl | H |
| 15 | CHO | H | (CH₂)₂COOH | Cl | H |
| 16 | CHO | H | (CH₂)₃COOH | Cl | H |
| 17 | CHO | H | (CH₂)₄COOH | Cl | H |
| 18 | CHO | H | CH₂COOCH₃ | Cl | H |
| 19 | CHO | H | Nicotinoyl | Cl | H |
| 20 | CHO | H | Benzoyl | Cl | H |
| 21 | CHO | H | Isonicotinoyl | Cl | H |
| 22 | CHO | H | OCH₂COOC₂H₅ | Cl | H |
| 23 | CHO | H | OCH₂COOCH₃ | Cl | H |
| 24 | CHO | H | OCH₂COOH | Cl | H |
| 25 | CHO | H | OCHCH₃COOC₂H₅ | Cl | H |
| 26 | CHO | H | OCHCH₃COOC₄H₉ | Cl | H |
| 27 | CHO | H | OCHCH₂CH₃COOC₂H₅ | Cl | H |
| 28 | CHO | H | O(CH₂)₃COOC₂H₅ | Cl | H |
| 29 | CHO | H | OCHCH₃COOH | Cl | H |
| 30 | CHO | H | O(CH₂)₃COOH | Cl | H |
| 31 | CHO | H | 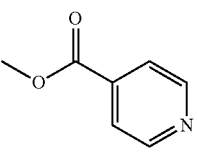 | Cl | H |
| 32 | CHO | H | OCOC₆H₄OCH₃ | Cl | H |
| 33 | CHO | H | OCOC₆H₄COOCH₃ | Cl | H |
| 34 | CHO | H | OCON(C₂H₅) | Cl | H |
| 35 | CHO | H | OCOCH₂OC₆H₄Cl | Cl | H |
| 36 | CHO | H | | Cl | H |
| 37 | CHO | H | 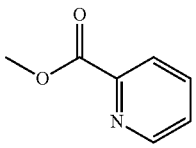 | Cl | H |
| 38 | CHO | H | OCH₃ | Cl | H |
| 39 | C₂H₂COCH₃ | H | H | Cl | O |
| 40 | CHO | H | CH₃CO | H | H |
| 41 | CHO | H | CH₃ | H | H |
| 42 | C₂H₂COCH₃ | H | CH₂COOH | Cl | O |
| 43 | CHO | CH₃CO | CH₃CO | Cl | H |
| 44 | C(OCH₃)₂ | H | CH₃CO | Cl | H |
| 45 | C(OCH₂CH₃)₂ | H | CH₃CO | Cl | H |
| 46 | C(OCH₂CH₃)₂ | H | CH₃ | Cl | H |
| 47 | C(O(CH₂)₃CH₃)₂ | H | CH₃ | Cl | H |

TABLE 2-continued

Formula 1

| Compound # | R₁ | R₂ | R₃ | R₄ | R₅ |
|---|---|---|---|---|---|
| 48 | (2-methyl-1,3-dioxan-2-yl) | H | CH₃ | Cl | H |
| 49 | CHO | H | O(CH₂)₃CH₃ | Cl | H |
| 50 | CHO | H | OCH₂CH₃ | Cl | H |
| 51 | CHO | H | OCH₂CHCH₂ | Cl | H |
| 52 | CO₂H | H | H | Cl | H |

TABLE 3

Formula 2

| Compound # | R₁ | R₂ | R₃ |
|---|---|---|---|
| 53 | Cl | H | H |
| 54 | H | H | H |
| 55 | Cl | H | OH |
| 56 | Cl | H | OAc |
| 57 | Cl | CH₃ | H |
| 58 | Cl | CH₃CO | H |
| 59 | H | CH₃ | H |
| 60 | H | CH₃CO | H |
| 61 | Cl | H | OCO(CH₃)₂ |
| 62 | Cl | H | OCOCH₂C(CH₃)₂ |

Genetically Engineered Cells

In certain embodiments, the invention relates to in vitro cultures of differentiating mammalian myoblasts (e.g., human primary myoblasts or mouse C2C12 myoblasts) in which the splicing factor hnRNP L is downregulated.

RNA silencing agents have received particular interest as research tools and therapeutic agents for their ability to knock down expression of a particular protein with a high degree of sequence specificity. The sequence specificity of RNA silencing agents is particularly useful for allele-specific silencing of dominant, gain-of-function gene mutations.

In certain embodiments, the instant invention provides short hairpin RNA (shRNA) capable of mediating RNA silencing of hnRNP L with enhanced selectivity. shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. The shRNAs of the invention are artificial constructs based on these naturally occurring pre-miRNAs, but which are engineered to deliver desired RNA silencing agents. By substituting the stem sequences of the pre-miRNA with sequence complementary to the target mRNA, a shRNA is formed. The shRNA is processed by the entire gene silencing pathway of the cell, thereby efficiently mediating RNAi.

shRNA molecules include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are preferably about 15 to about 50 nucleotides in length. In certain embodiments, the two stem portions are about 18 or 19 to about 21, 22, 23, 24, 25, 30, 35, 37, 38, 39, or 40 or more nucleotides in length. In certain embodiments, the length of the stem portions should be 21 nucleotides or greater. In certain embodiments, when used in mammalian cells, the length of the stem portions should be less than about 30 nucleotides to avoid provoking non-specific responses. In certain embodiments, in non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs may differ from natural pre-miRNA sequences by modifying the loop sequence to increase or decrease the number of paired nucleotides, or replacing all or part of the loop sequence with a tetraloop or other loop sequences. Thus, the loop in the shRNAs can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the invention include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA, for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR, provided said portion is distant from the site of the gain-of-function mutation. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Exemplary RNAi Agents, Nucleic Acid Molecules, Recombinant Nucleic Acid Constructs and Vectors, and Methods In certain embodiments, the invention relates to a RNA interference (RNAi) agent capable of reducing, attenuating, or abolishing the production of hnRNP L in a cell, wherein the cell is a mammalian myoblast or a mammalian myotube.

In certain embodiments, the invention relates to any one of the aforementioned RNAi agents, wherein the RNAi agent is selected from the group consisting of RNAi nucleic acid molecules, RNAi nucleic acid analogue molecules, short interfering nucleic acids, short interfering nucleic acid analogues (siNA), short interfering RNA, short interfering RNA analogues (siRNA), double-stranded RNA, double-stranded RNA analogues (dsRNA), micro-RNA, micro-RNA analogues (miRNA), short hairpin RNA, and short hairpin RNA analogues (shRNA).

In certain embodiments, the invention relates to any one of the aforementioned RNAi agents, wherein the RNAi agent is shRNA.

In certain embodiments, the invention relates to any one of the aforementioned RNAi agents, wherein the RNAi agent is configured to target the hnRNP L gene of the mammalian myoblast or the mammalian myotube, or a variant of the hnRNP L gene of the mammalian myoblast or the mammalian myotube having at least about 80%, about least about 85%, at least about 90%, at least about 95%, at least about 98%, or at least about 99% sequence identity to the hnRNP L gene of the mammalian myoblast or the mammalian myotube.

Human hnRNP L comes in 2 isoforms,
Transcript variant 1 (2,129 bp linear mRNA, Accession: NM_001533.2)
Transcript variant 2 (1,895 bp linear mRNA, Accession: NM_001005335.1)
Protein variant a (589 aa, Accession: NP_001524.2) (See FIG. 13)
Protein variant b (456 aa, Accession: NP_001005335.1) (See FIG. 13)

Importantly, both a and b Protein Isoforms Co-Precipitate with MBNL1 in Vitro.

In certain embodiments, the invention relates to a method of attenuating hnRNP L gene expression in a cell, comprising the steps of:
  contacting a plurality of cells with a recombinant nucleic acid construct or vector, wherein the recombinant nucleic acid construct or vector encodes any one of the aforementioned RNAi agents, and wherein the cells are mammalian myoblasts, thereby producing a subset of cells that express the RNAi in an amount sufficient to attenuate hnRNP L gene expression in the subset of cells.

In certain embodiments, the invention relates to any one of the aforementioned methods, wherein the recombinant nucleic acid construct or vector is a lentiviral vector; and the cells are contacted with the lentiviral vector at a viral titer of about $2 \times 10^8$ TU/mL.

In certain embodiments, the invention relates to a method comprising the steps of:
  contacting a plurality of cells with a recombinant nucleic acid construct or vector, wherein the recombinant nucleic acid construct or vector encodes any one of the aforementioned RNAi agents, and wherein the cells are mammalian myoblasts, thereby producing a subset of cells that express the RNAi in an amount sufficient to attenuate hnRNP L gene expression in the subset of cells;

selecting the subset of cells, thereby forming a selected subset of cells;

exposing the selected subset of cells to a compound; and analyzing the progression of differentiation of the mammalian myoblasts into mammalian myotubes.

In certain embodiments, the invention relates to any one of the aforementioned methods, wherein the recombinant nucleic acid construct or vector is a lentiviral vector; and the cells are contacted with the lentiviral vector at a viral titer of about $2\times10^8$ TU/mL.

In certain embodiments, the invention relates to any one of the aforementioned methods, wherein the selected subset of cells is exposed to the compound on about day 2 of differentiation of the mammalian myoblasts into mammalian myotubes.

In certain embodiments, the invention relates to any one of the aforementioned methods, wherein the progression of differentiation of the mammalian myoblasts into mammalian myotubes is analyzed on or after day 4 of differentiation of the mammalian myoblasts into mammalian myotubes.

In certain embodiments, the invention relates to any one of the aforementioned methods, wherein the progression of differentiation of the mammalian myoblasts into mammalian myotubes is analyzed on day 4 of differentiation of the mammalian myoblasts into mammalian myotubes.

In certain embodiments, the invention relates to any one of the aforementioned methods, wherein a plurality of subsets of cells is exposed to a plurality of different compounds in parallel.

In certain embodiments, the invention relates to any one of the aforementioned methods, wherein the progression of differentiation of the mammalian myoblasts into mammalian myotubes is analyzed by microscopy.

In certain embodiments, the invention relates to any one of the aforementioned methods, wherein the compound is a small molecule, a peptide, a natural product, or a plant extract.

In certain embodiments, these cultures serve as a sensitive high throughput screen to identify hit compounds or derivatives that rescue/enhance muscle function. In certain embodiments, the hit compounds serve as templates for the development of novel therapeutics targeting muscle disease in mammals. In certain embodiments, the invention relates to a compound, wherein the compound rescues or enhances myotube formation as identified in any one of the aforementioned methods. In certain embodiments, the invention relates to a compound identified by any one of the aforementioned methods.

EXPERIMENTAL

Smooth male mutant flies were collected at 1 day of age, and maintained either on vehicle alone, or on one preselected ascochlorin derivative (2 mM solution in vehicle). After 7 days of treatment, the flies were collected and assessed using a negative geotaxis assay (Allikian, M. J. et al., Reduced life span with heart and muscle dysfunction in *drosophila* sarcoglycan mutants, *Hum Mol Genet.*, 2007, 16:2933-2943; Naimi, B. et al., A tropomyosin-2 mutation suppresses a troponin i myopathy in *drosophila, Mol Biol Cell,* 2001, 12:1529-1539) as follows: flies were gently tapped to the bottom of an empty vial, thus prompting a climbing response. The number of flies crossing a 2 cm-high threshold line in 10 seconds was recorded. Percent *Drosophila* crossing the threshold was used as an index of locomotor activity. Vehicle exposed flies: n=12; drug treated flies: n=14. Each repeat showed the average of three consecutive recordings. Three repeats were performed at 2 minute intervals on the same group of flies (nine values total/pharmacologic exposure).

We have demonstrated that in vivo down regulation of the *Drosophila* homolog of hnRNP L, SMOOTH, leads to marked degeneration of the muscles in adult flies. The muscle defects are highly reminiscent of lesions observed in patients affected with muscular dystrophy. As in Duchenne muscular dystrophy (DMD) or myotonic dystrophy (DM) patients, the muscle dystrophy is associated with a marked reduction in motor function, as well as in longevity. Smooth mutation-induced muscle dystrophy is triggered when down regulation of smooth is specifically targeted to the mesoderm, highlighting an important intrinsic role for this splicing factor in muscle physiology. (Draper, I. et al., The evolutionarily conserved RNA binding protein smooth is essential for maintaining normal muscle function, *Fly (Austin)*, 2009, 3:235-246). HnRNP L is abundantly expressed in C2C12 mouse myoblasts and myotubes, as well as in rat primary cardiomyocytes (hnRNP L mRNA levels were assessed by RT-PCR analysis, and protein levels were assessed by Western blot analysis, not shown).

Our data indicates that ascochlorin and structurally related compounds hold promise as potential therapeutics for the treatment of muscle degeneration/wasting linked to muscular dystrophy, myopathy, and aging. This effect might be mediated by an increase in the levels of the RNA binding protein hnRNP L and/or hnRNP L targets (some of them already associated with muscle disease, e.g., BIN1), with or without effect on mRNA splicing. These drugs may also be utilized to enhance normal muscle function.

Example 1

HTS hnRNP L Levels in C2C12 Myoblast Cell Line

The aim of the current study is to quantify hnRNP L transcript levels in C2C12 myoblasts in response to drug administration (vs. corresponding levels measured in untreated myoblast), utilizing real time PCR. Compounds that induce differential hnRNP L expression will be considered as candidate template chemical structures for the development of novel therapeutics to treat muscle disorders.

A. Design of qPCR Primers Corresponding to Mouse hnRNP L.

A1. Template Mus *musculus* heterogeneous nuclear ribonucleoprotein L (Hrnpl), mRNA, 2,142 bp linear mRNA. Accession: NM_177301.5

Figure 2:
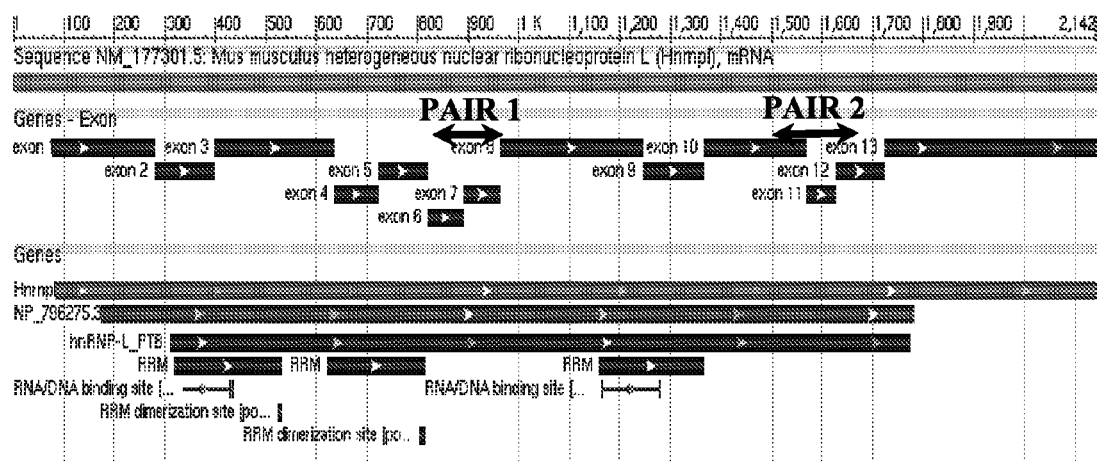
FIG. 2 shows the position of the two amplicons that are amplified by qPCR primer pair 1 and primer pair 2 (red bars) on the corresponding mouse hnRNP L mRNA sequence graphic (from GenBank).

A2. Primers. hnRNP L qPCR primers were designed utilizing the NCBI program http://www.ncbi.nlm.nih.gov/tools/primer-blast/, with the following criteria: amplicon size=90-150 nt, and exon junction crossed. The two pairs described in the Table 4 below are specific to input template, i.e., no other targets were found in the database. The corresponding amplicons are shown on the graphic of hnRNP L mRNA sequence, in FIG. 2.

TABLE 4

|  | Primer sequence | strand | length | start | stop | Tm | Exon junction |
|---|---|---|---|---|---|---|---|
| PAIR 1 91 nt amplicon | | | | | | | |
| Exon 6_Forward (mhnE6F) | aggtgaccctggcagt aacccc | Plus | 22 | 891 | 912 | 59.85 | |
| Exon 7/8_Reverse (mhnE6R) | cccaccatggggccct ccatat | Minus | 22 | 981 | 960 | 59.78 | 964/ 965 |
| PAIR 2 147 nt amplicon | | | | | | | |
| Exon 10_Forward (mhnE10F) | ccgcatccagcaccct agcaa | Plus | 21 | 1494 | 1514 | 59.18 | |
| Exon 11/12_Reverse (mhnE10R) | gagctccgctcgcttttg cct | Minus | 21 | 1640 | 1620 | 60.05 | 1627/ 1628 |

B. C2C12 Cell Culture.

The C2C12 mouse myoblast cell line is routinely cultured in the laboratory, as previously described in the literature (Dalkilic I. et al., *Loss of FilaminC (FLNc) Results in Severe Defects in Myogenesis and Myotube Structure*, MCB, 2006). The cells will be grown in a 96-well plate (high throughput) format. Sub-confluent C2C12 cultures grown in medium supplemented with 10% fetal calf serum maintain the myoblast state. By comparison, switching C2C12 cells that are ~80% confluent to medium supplemented with 2% horse serum for six days results in myotube formation. HnRNP L levels will be first assessed in myoblast (in the presence, or absence, of the drug). Follow-up analysis will be done using differentiated myotubes.

C. Optimization of the RT-PCR Assay.

C1. Preparation of Total RNA/cDNA from C2C12 Cultured Cells

RNA is prepared at Day 1 after plating. At this time, all cells are in the myoblast stage (typically the first myotubes appear at Day 3, most at Day 7). Total RNA is isolated either with RNeasy Mini kit 50/Qiagen Cat#74104 (prep1, [RNA]=0.5 µg/µl), or with RNA STAT-60/Tel-Test, Inc. (prep 2, [RNA]>1 µg/µl). Reverse transcription (RT) reaction was carried out to generate complementary DNA where [cDNA]=50 ng/µl (use 2 µl cDNA/one regular PCR reaction).

C2. Generation of Standard Curves to Assess Amplification Accuracy Over a Range of [cDNA], as Well as to Measure hnRNP L qPCR Primer Efficiency and Specificity.

Methodology

The primer stocks are prepared at 10 pm/µl. The qPCR cocktail is calculated to accommodate (n+1) reactions, e.g., n=7 (6 cDNA serial dilutions, 1 no-template control)+1 extra volume.

| Per Rxn | per (n + 1) Rxs | |
|---|---|---|
| 0.6 µL | (n + 1) × 0.6 µL | Forward primer (10 pm/µl stock: 300 nM final) |
| 0.6 µL | (n + 1) × 0.6 µL | Reverse primer (10 pm/µl stock: 300 nM final) |
| 6.8 µL | (n + 1) × 6.8 µL | dH$_2$O |
| 10 µL | (n + 1) × 10 µL | SYBR 2x Mastermix |
| 18 µL | (n + 1) × 18 µL | |

18 µL of cocktail is aliquoted per well. 2 µL of water (no-template control), or of the appropriate cDNA dilution (1×, 4×, 16×, 64×, 256×, 1024× . . . ), is added to each well. The following amplification profile is run:

95° C.: 10 mn
40×—95° C.: 5 s
63° C.: 20 s

Dissociation Curve

Figure 3:
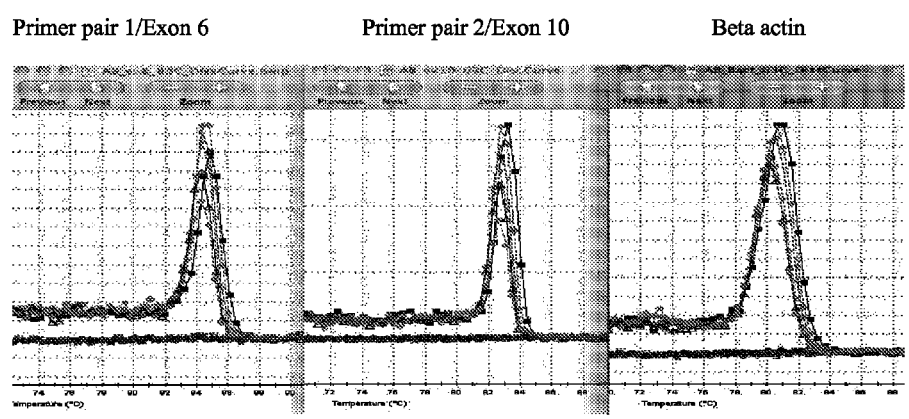
FIG. 3 shows melting curves generated for hnRNP L primer pair 1, hnRNP L primer pair 2, and β-actin.

A melting curve was generated for each primer pair utilized (i e, hnRNP L primer pair 1, hnRNP L primer pair 2, and β-actin). Results show that each pair generates a single melting curve (at or above 80° C.), indicating template specificity. (FIG. 3)

Figure 4:
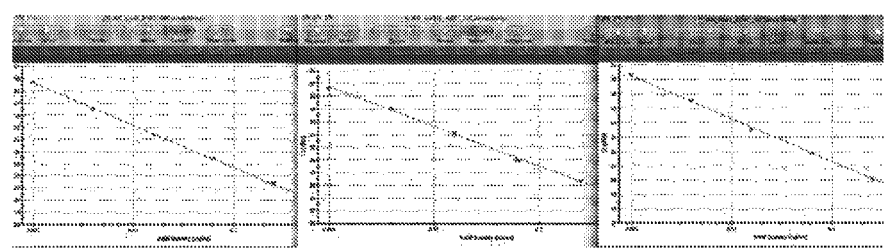
FIG. 4 shows a standard curve for hnRNP L primer pair 1, hnRNP L primer pair 2, and β-actin.

In addition, for each primer pair, a standard curve is generated using serial dilutions of the cDNA (i.e., 1×, 4×, 16×, 64×, 256×, 1024× . . . ). In each case, the amplification efficiency falls in the 100%+10% range, indicating primers specificity. (FIG. 4) Typically, [cDNA] that generate cycle thresholds (Ct) between 20-30 are optimal for qPCR analyses.

D. Adaptation of the Approach to a 96-Well Plate, HTS Format.

D1. Preparation of Total RNA from C2C12 Cultured Cells

High quality, concentrated and purified total RNA (up to 5 µg/well; [RNA]=0.2 µg/µL, 25 µL/well) will be isolated using the ZR-96 Quick-RNA™ technology (Zymo research, Catalog Nos. R1052 & R1053).

D2. RT-PCR Reaction

PCR reactions will be performed using the QIAGEN OneStep RT-PCR Kit (Qiagen, cat. nos. 210210, 210212), which allows fast and easy RT-PCR setup. Reverse transcription and PCR are carried out sequentially in the same tube. All reagents required for both reactions are combined in one tube during setup, and the thermal cycler program is started.

| OneStep RT-PCR Kit contents | Features |
|---|---|
| HotStarTaq ® DNA Polymerase | Highly specific products |
| Omniscript ® and Sensiscript ® RT | Wide range of RNA amounts (1 pg-2 µg) High sensitivity |
| OneStep RT-PCR Buffer | Minimal optimization needed No inhibition of PCR by reverse transcriptases |
| Q-Solution | Facilitates amplification of GC-rich templates |

(Table as shown in the QIAGEN ® OneStep RT-PCR Kit Handbook)

E. Drug Screen (Utilizing the Established High-Throughput Assay Described Above).

C2C12 myoblast cell cultures will be treated with ascochlorin, or with derivative compounds (e.g., ascofuranone), as described by Kang and colleagues using the human osteosarcoma U2OS cell line (Kang J H et al., *Proteome Analysis of Responses to Ascochlorin in a Human Osteosarcoma Cell Line by 2-D Gel Electrophoresis and MALDI-TOE MS*, J. Proteome Research, 2006). Alternatively, established libraries of small molecules (e.g., The Prestwick Chemical Library® of 100% FDA approved drugs) will be screened for effects on hnRNP L levels. (Kopin A S et al., *Identification of a series of CCK-2 receptor nonpeptide agonists: sensitivity to stereochemistry and a receptor point mutation*, PNAS USA, 2003).

The ability of a drug to induce either a significant increase, or a decrease, in hnRNP L levels will be assessed. As an initial threshold, compounds that induce a ≥4-fold difference in hnRNP L transcript levels (as assessed by a ≥2-fold cycle threshold, Ct, difference by real time PCR, vs. levels in untreated cells) will be further characterized. Independent biological replicates, and corresponding dose response curves, will be obtained/analyzed. Complementary follow-up studies will include the quantification of hnRNP L protein levels in treated, vs. untreated, C2C12 myoblasts.

Example 2

Identification of Novel Therapeutics for Muscle Diseases that Target hnRNP L Pathways Using a Combination of In Vitro Screens and In Vivo Screens An assay was designed to identify compounds that enhance the survival of myotubes that would otherwise degenerate and die following hnRNP L gene silencing. HTS is done utilizing a human myoblast cell line (from a healthy individual) that downregulates hnRNP L via expression of a lentiviral vector encoding small interfering hnRNP L RNAs. We have shown that hnRNP L deficient myoblasts display marked differentiation defects as follows: although hnRNP L KD myoblasts proliferate normally and differentiate into early myotubes (Day 2 differentiation), newly formed mature myotubes (Day 4), rapidly break down leaving in the culture residual myoblasts (FIGS. 5 and 6). Using the hnRNP L KD cell line, pharmacological compounds that improve myotube survival and maintenance are identified. Hit compounds are further assessed using a combination of in vitro and in vivo confirmatory assays and secondary screens, including (i) assessment of drug-induced differential hnRNP L expression, (ii) rescue of phenotypes displayed by cultured diseased (e.g., DMD, DM1) myotubes, and (iii) in vivo assessment of drug effects on muscle phenotypes displayed by relevant model organisms (e.g., mutant *Drosophila*, mouse models). Promising compounds are considered as template chemical structures for the development of novel therapeutics to treat muscle disorders and/or sarcopenia.

A. Establishment of a Human Myoblast Cell Line that Expresses Interfering hnRNP L RNA.

A1. Human Myoblast Cell Isolation and Culture.

Human skeletal muscle-derived myoblasts were isolated and cultured using well-established protocols (Alexander et al., *Skeletal Muscle*, 2011; Gharaibeh et al., *Nature Protocols*, 2008). Sub-confluent cultures grown in medium supplemented with 10% fetal bovine serum maintained the myoblast state. By comparison, switching cells that are ~90% confluent to medium supplemented with 2% FBS for 7-14 days resulted in myotube formation.

A2. Lentivirus-Mediated Silencing of hnRNP L in Normal Human Myoblasts.

Lentiviral vectors expressing small hairpin RNA (shRNAs) can be used to downregulate gene expression in cultured muscle cells. This approach was applied to hnRNP L gene silencing in human myoblasts/myotubes. The design and cloning of the corresponding lentiviral vector (shHNRNP L), as well as of the control vector (shLuc, the hairpin RNA targets the luciferase gene) were done according to established methodologies (Alexander et al., *Skeletal Muscle*, 2011; Tiscornia et al., *Nature Protocols* 2006). Lentiviral infections were performed at a viral titer of approximately $2 \times 10^8$ TU/mL. Downregulation of hnRNP L expression in differentiating myoblasts resulted in rapid collapse of the myotubes at Day 4 differentiation (FIG. 5, Day 4, shHNRNP L vs. shLuc controls).

The reserve myoblasts that remained in the shHNRNP L culture at Day 4 later differentiated into few myotubes that were disorganized (FIG. 6, Day 14, arrow). This phenotype is reminiscent of that described for cultured myotubes derived from patients with muscular dystrophy (e.g., DM1, Loro et al., *Cell Death and Differentiation*, 2010).

Figure 7:
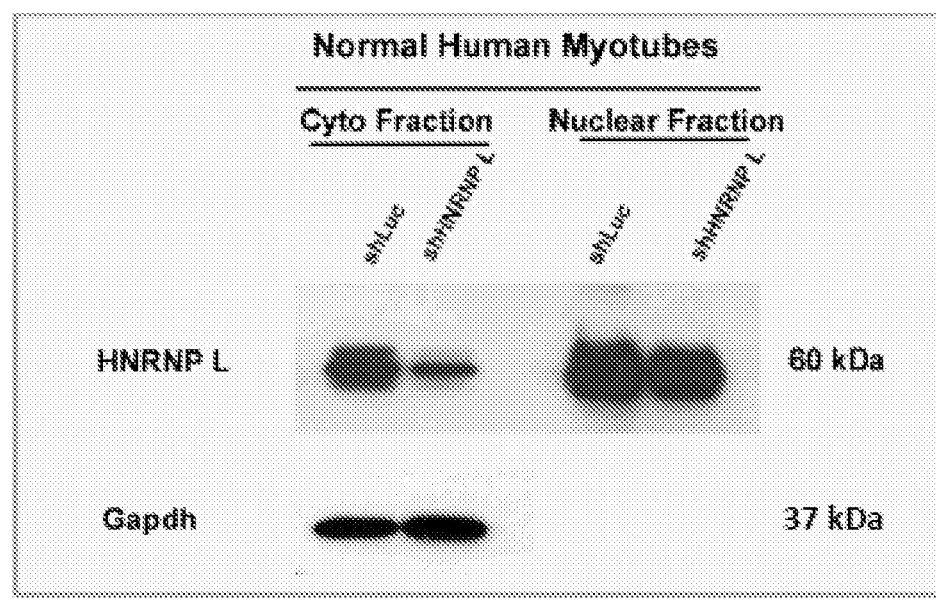
FIG. 7 depicts gels taken at day 7 of differentiation for myotubes that express the shHRNP L virus. The results show a decrease in hnRNP L protein levels, in both the whole cell lysate (Cyto fraction), and nuclear fraction (vs. normal levels in shLuc control virus-expressing myotubes). Gapdh staining demonstrates cytoplasmic lysate loading.

ShHNRNP L knockdown efficiency was determined by Western blot analysis of myotubes at Day 7 Differentiation (utilizing a monoclonal anti-hnRNP L antibody, FIG. 7).

B. Drug Screens

Myoblast cell lines (that stably express the shHNRNP L lentiviral construct) can readily be grown in a 96-well, or 384-well plate format, amenable to HTS.

Differentiating shHRNP L myoblast cell cultures will be treated with ascochlorin, or derivative compounds (e.g., ascofuranone), as described by Kang and colleagues using the human osteosarcoma U2OS cell line (Kang J H et al., *Proteome Analysis of Responses to Ascochlorin in a Human Osteosarcoma Cell Line by 2-D Gel Electrophoresis and MALDI-TOE MS*, J. Proteome Research, 2006). Compound treatment will be done at Day 2 Differentiation, prior to the observed myotube degeneration/death that occurs at Day 4.

Alternatively, established chemical libraries of small molecules (e.g., The Prestwick Chemical Library® of 100% FDA approved drugs), or larger libraries (public domain or proprietary), will be screened for partial or complete rescue of the differentiation defects displayed by hnRNP L-deficient myoblasts (FIG. 12). These libraries include a small molecule library, and a natural product library, both available at the Tufts Medical Center Molecular Pharmacology Research Center (MPRC, Dr. A. Kopin Director). In addition, we will screen the library of FDA-approved 'bioactive' drugs from the Chemical Biology/Novel Therapeutics (CB/NT) Outreach Lab at the Broad Institute.

The shHNRNPL myoblasts will be seeded in the 384-well plates and grown until 90% confluence (two days). The cells will be subsequently differentiated by changing the media from 20% to 2% FBS. Pharmacological treatment will be done at Day 2 differentiation, when the nascent myotubes form. Each compound will be added at $10^{-5}$ M (30 nL/100 µL media in each well, the final DMSO concentration is 0.33%). Treatment with DMSO solvent only (no drug) will provide controls. At Day 4 the cells will be washed to remove the debris, and the effect of the drug on myotube survival will be assessed. An automated imaging program will be used to detect drug-induced rescue of multi-nucleated myotubes myotubes. Negative controls (treated with DMSO, no drug) will show only residual myoblasts, reflecting the degenerative phenotype due to hnRNP L KD. Positive control (shLuc myoblast, hnRNP L levels are normal) show multi-nucleated myotubes.

Automated Imaging System. A high throughput phenotype imaging and analysis program, developed at Tufts University Study Center on the Immunogenetics of Infectious Disease (SCIID) to assess myoblast to myotube differentiation in 96-well plates, will be utilized. The strategy uses the high content based ImageXpress Micro Imaging System (Molecular Devices Corporation), with modifications to the MetaXpress program. This workflow can assess each myotube, identified by Troponin T immunostaining, for the following cellular parameters: area, perimeter length, breadth, shape factor, and integrated intensity. Nuclear parameters (e.g. total number of nuclei and nuclear area) also measured. The program will be adapted to a 384-well plate format.

The objectives of the pilot screens are as follows: (1) establishment of assay quality (determination of z'-factors, inter-well and day-to-day variability), (2) potential identification of hits that will be followed as discussed below, and (3) validation of the assay to a point where it is suitable to HTS of a much larger library.

C. In Vitro and In Vivo Confirmatory Assays and Secondary Screens.

Pending positive results, the activity/toxicity of hits/ derivative of hits will be further assessed in in vitro and in vivo confirmatory assays, and secondary creens. For each "hit", independent biological replicates, and corresponding dose response curves will be obtained/analyzed. The follow-up studies will include:
1. Western blot analysis of hnRNP L protein levels and/or real-time PCR quantification of hnRNP L mRNA levels, in drug treated, vs. untreated, shHNRNP L myoblasts.
2. Assessment of drug effects on primary myoblast cell lines isolated from DM1 muscle tissue (see Example 3). The ability of the drug to rescue/improve the phenotype displayed by DM1 myotubes (e.g. disorganization, low abundance), will be assessed.
3. The in vitro primary screen will be followed by in vivo assessment of candidate hits utilizing a whole animal model (i.e. *Drosophila*). We have previously shown that *Drosophila* that downregulate smooth, the fly homolog of mammalian hnRNP L, display shortened lifespan and marked muscle degeneration. The in vivo studies using smooth-deficient flies expedite assessment of delivery, activity and toxicity of any candidate compound identified in the primary screen. In parallel, compounds will also be tested for their ability to rescue the phenotypes of established fly models of DM1.

Additional Considerations (i) Library compounds that are cytotoxic will act against the selection in our screen (i.e. compounds are selected for their ability to restore/improve survival of muscle fibers). Toxic drugs will thus 'self-eliminate'. (ii) A hit compound may improve/rescue myofiber viability via a mechanism which is either hnRNP L-dependent, or -independent (i.e. the drug may not necessarily affect hnRNP L levels). In either case, compounds will provide promising templates for the development of future therapeutics that lessen DM1 associated-muscle degeneration. (iii) Backup screen: In the event that the original phenotypic readout (i.e. survival of hnRNP L-deficient Day 4 myotubes) is too stringent to enable identification of hits, the libraries will be re-screened using as readout the milder phenotype displayed by hnRNP L-deficient Day 14 myotubes. Day 14 fibers are observed in the culture, albeit less numerous and disorganized compared to controls. This less stringent assay may enable the identification of effective drugs that would otherwise be missed in the initial screen. (iv) We are aware that elevating the levels of a global splicing factor (i.e. hnRNP L) might have deleterious physiological consequences. Preliminary studies from our lab, as well as reports in the literature, suggest however that overexpression of smooth (the fly homolog of hnRNP L) in *Drosophila*, or of hnRNP L in *Xenopus*, is well-tolerated by the organism. Smooth-overexpressing flies display normal gross morphology, locomotor activity, fertility and lifespan. Notably, overexpression of MBNL1 in mice had also no apparent adverse effect.

Collectively, our studies open the possibility of identifying novel candidate pre-therapeutic leads that could be further developed for the treatment of muscle diseases, including myotonic dystrophy. In future studies, the biodistribution, activity/efficacy and toxicity of the most promising candidate drugs will be examined in rodent models of DM1.

Example 3

Characterization of hnRNP L Function in Normal Human and DM1 Muscle Cell Lines

Figure 8:
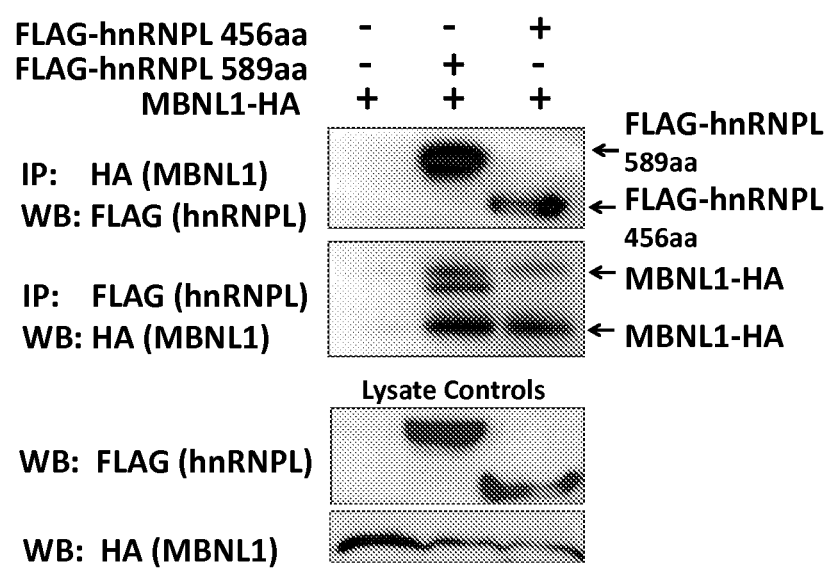
FIG. 8 depicts HNRNP interacting with MBNL1. Top panel Co-immunoprecipitation (co-IP) of FLAG-tagged hnRNP L isoforms (589 aa), or (456 aa), with HA-tagged-MBNL1. Immunoprecipitation is performed with HA-beads (MBNL1-HA), and immunoblot with anti-FLAG antibody. Input lysate control immunoblot detecting the anti-HA antibody is shown at bottom. Middle panel. Reverse co-IP using FLAG-beads (HNRNP L). Of note, multiple MBNL1 isoforms are pulled. Control immunoblot detecting the anti-FLAG antibody is shown at bottom. Abbreviations, IP: immunoprecipitation; WB: Western blot.

HnRNP L is a multifunctional RNA-binding protein involved in mRNA alternative splicing, export and stability. This conserved splicing factor is expressed in a wide range of tissues, including muscle. Decreased level of smooth (the fly homolog of hnRNP L) in *Drosophila*, or of hnRNP L in zebrafish results in marked muscle defects. In addition, we and others have recently shown that hnRNP L physically interacts with MBLN1 (FIG. 8), one of the known RBPs that underlies DM pathogenesis. This led us to hypothesize that hnRNP L plays an important role in both normal and myotonic human muscle cells. To begin to define the molecular function of hnRNP L in human skeletal muscle, we propose a combination of in vitro cell culture analyses, using banked normal and DM1 muscle cells in a series of overexpression and knockdown of hnRNP L experiments. Of note, three DM1 myoblast cell lines (#9886, 10008 and 10009) were obtained from the Telethon Cell Bank, and established in the Kunkel lab.

A. The expression profile of hnRNP L in normal vs. DM1 human myoblasts and myotubes will be determined (differentiation Day 0 through Day 14). The ratio of known hnRNP L isoforms and subcellular localization will be compared.

Figure 9:
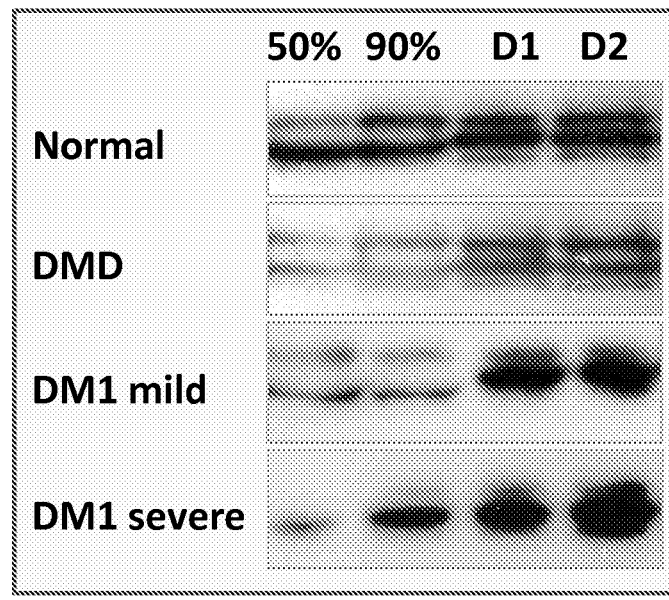
FIG. 9 depicts HnRNP L expression in proliferating and differentiating, normal and diseased, human myoblasts. Western Blot analysis (using the 4D11 monoclonal anti-hnRNP L antibody, Sigma) shows a doublet at ~60 kDa. The level of the lower hnRNP L band in the doublet appears elevated (as a ratio of the higher band), in differentiated DM1 (mild, or severe, phenotype) muscle cells, but not in DMD (Duchenne muscular dystrophy) cells, (compared to normal muscle cells). Abbreviations, %: percent confluence; D: differentiation day.

The ratio of known hnRNP L isoforms and subcellular localization will be determined during myogenic differentiation (days 0 through 14). The levels of hnRNP L isoforms (variant 1: 589 aa, 64 kDa vs. variant 2: 456 aa, 50 kDa) will be determined by quantitative RT-PCR (using isoform-specific primers), and Western blot analysis (using the 4D11 mouse monoclonal, Sigma), in normal and DM1 myoblasts and myotubes. The two hnRNP L RNA isoforms differ in their 5' UTR/start codon region. Variant 1 is the predominant isoform in all tissues (including muscle); whereas we have only seen potential evidence of the shorter hnRNP L during fetal myogenesis (data not shown). We will also determine the subcellular localization of hnRNP L (cytoplasmic vs. nuclear) via immunohistochemical analysis as described before. Of note, preliminary analysis of hnRNP L expression in differentiating normal and diseased human myoblasts shows a moderate increase in DM1, vs. normal, muscle cells (FIG. 9). This is reminiscent of findings recently published for another RBP, Staufen1, which up-regulation is postulated to be protective in DM1.

B. The effects of lentivirus-mediated hnRNP L knockdown, or overexpression, on myogenic proliferation/differentiation will be assessed, in normal vs. DM1 human cell lines. The effects on cell morphology/organization, as well as on the expression of myogenic/myofibrillar markers, will be assessed. In addition, we will analyze the expression of exons that are misspliced in DM1 patients (e.g. DMD exon 71, IR exon 11) to define the role of hnRNP L in this process.

Lentiviral vectors expressing small hairpin RNA (shRNAs) are routinely used to downregulate (KD) gene expression, or full-length cDNA to overexpress (OE) gene expression, in cultured muscle cells. Following lentiviral-mediated KD, or OE, of hnRNP L levels, the analyses (i)-(iv), will be performed.

(i) Myoblast proliferation and differentiation will be measured by MTS assay, as previously described. Proliferation rate of the myoblasts over a 5-day period will be expressed as a ratio of hnRNP L levels (as determined by Western blot).

(ii) Myogenic differentiation rates will be determined via assessment of myogenic fusion indices based on the expression levels myosin heavy chain (MyHC. a well-characterized myogenic differentiation marker).

(iii) Myogenic fusion indices will be determined using the ratio of MyHC to nuclei per field, and per multi-nucleated myotube. Additional differentiation markers (e.g. myogenin, Mef2c, and dystrophin) will be analyzed in Western blot and immunostaining, to determine the rate of myogenic differentiation following hnRNP L OK or KD.

Figure 10:
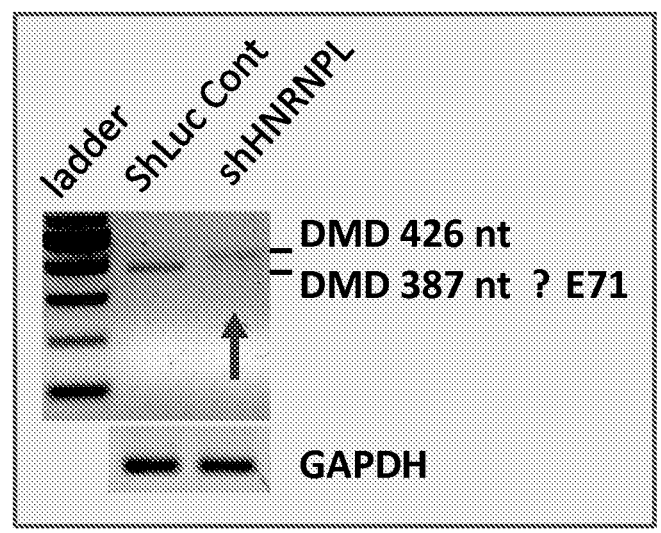
FIG. 10 depicts that DMD exon 71 is aberrantly spliced in hnRNP L-deficient myotubes. Total RNA was prepared from Day 2 differentiation myotubes that express either the shHNRNPL (i.e. hnRNP L KD), or the control shLuc, lentivector. RT-PCR analysis was performed using the same primer pair that was utilized by Nakamori et al. to demonstrate missplicing of DMD E71 in human DM1 muscle. Exclusion of the exon results in the generation of the shorter Δ E71 DMD isoform.

(iv) The alternative splicing of exons that are known to be aberrantly processed in DM1 patients will be assessed. To date, these misplicing events correspond to ~28 RNA target. Our preliminary data show that DMD (dystrophin) exon 71 is aberrantly processed in hnRNP L KD (vs. normal) muscle cells (FIG. 10). DMD exon 71 is known to be aberrantly spliced in DM1.

The proposed experiments will begin to define the role hnRNP L in regulating normal muscle cell growth, differentiation, proliferation and viability. In addition the analysis of hnRNP L-dependent processing of exons that are known to be misspliced in DM1 (e.g. DMD exon 71, FIG. 10), will potentially implicate this factor in DM1 pathogenic processes. Finally, these studies will provide a baseline of information on which to better understand the effects of candidate pre-therapeutic leads, as identified in our screen.

C. The spectrum of RNA targets processed by hnRNP L in normal human muscle cells will be defined. We will carry out high throughput RNA Sequencing (RNA-seq) of total RNA extracted from hnRNP L-silenced (vs. control) Day 2 myotubes. Comparison will be made between misplicing events resulting from hnRNP L knockdown and those known to be associated with DM1 (potentially implicating hnRNP L in the pathogenesis of these events).

Previous reports in the literature have demonstrated that hnRNP L is a key regulator of alternative splicing that can promote either the inclusion, or the exclusion, of tissue-specific exons. Interestingly, hnRNP L binding motifs were shown to be enriched in alternative splicing events that are associated with myogenic differentiation. We recently carried out a bioinformatic analysis of a compendium of known human alternative splicing events to identify sequences that include the hnRNP L binding motif, and are expressed in skeletal muscle and/or the heart. This analysis revealed 46 conserved putative targets of hnRNP L in muscle and the heart. Importantly, the list includes nine targets, APP, BIN1, DMD, DTNA, MAPT, MEF2A, PPP2R5C, SORBS1 and TTN, which are known to be aberrantly spliced in DM1 patients. This is a remarkably high number, given that to date, a total of less than 30 splicing defects have been confirmed in DM1 patients. These findings, together with data from our lab and others showing that hnRNP L and MBNL 1 form a complex (FIG. 8), provide a strong rationale to define the full complement of RNA targets that are processed by hnRNP L in human muscle. To achieve this objective, we propose to utilize genome-wide RNA based deep-sequencing (RNA-Seq), of total RNA prepared from normal human muscle cells in which hnRNP L is down-regulated (KD, vs. controls). Although hnRNP L KD myoblasts differentiate into nascent myotubes, hnRNP L KD multi-nucleated myotubes degenerate rapidly (FIG. 5 and FIG. 11). Our in vitro assay provides a unique system to define the global changes in hnRNP L-dependent alternative splicing that affect the formation and/or maintenance of differentiated muscle cells, with potential relevance to DM1 pathology.

Total RNA will be isolated from early (i.e. differentiation Day 2) myotubes that express the hsHNRNPL interference construct (i e hnRNP L KD), as well as from Day 2 myotubes that express the hsLuc construct (i.e. controls). For each genotype, three independent RNA samples will be prepared. RNA-Seq will be carried out at the Tufts University Genomics Core (http://genomics.med.tufts.edu) under the supervision of Core manager, Dr. A. Tai, who is a consultant on the proposed project (please see letter of support). The Core offers investigators state of the art technologies for RNA-Seq analysis including (i) quality control of the input RNA (Agilent bioanalyzer) (ii) library preparation (TruSeq Stranded Total RNA Sample Prep Kit), (iii) sequencing (Illumina HiSeq 2000 using the TruSeq SBS Kit v3-HS chemistry), and (iv) data analysis (i.e. mapping, expression and splice variants analysis of the transcriptome) using the Galaxy server (galaxy.med.tufts.edu).

The proposed investigations will potentially unravel (i) early markers of the degenerative muscle process, and (ii) novel therapeutic targets for DM. Comparison will be made with candidate gene lists generated in previous transcriptome analyses of muscle isolated from DM1 patient, or from rodent models of DM1, to determine the common as well as distinct sets of genes/exons that are aberrantly processed following de-regulation of the splicing factors. The subset of targets that are both consistently misspliced across the analyses, and evolutionarily conserved, will be prioritized for further study. RT-PCR analysis will be performed (utilizing exon-specific primers) to confirm the differential splicing of the exon in hnRNP L-deficient, vs. control, myotubes. Although likely be beyond the timeline of this proposal, subsequent studies in *Drosophila* will offer an expedited means to begin to investigate the functional relevance of the new candidate targets in muscle physiology/disease. Future studies in human cell lines will focus on the most promising among these targets.

INCORPORATION BY REFERENCE

All of the cited U.S. patents, U.S. patent application publications, and PCT patent application publications designating the U.S., are hereby incorporated by reference in their entirety.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed.

What is claimed is:

1. A method of treating a muscle disease or improving muscle function, comprising the step of administering to a mammal in need thereof a therapeutically effective amount of an isoprenoid antibiotic.

2. The method of claim 1, wherein the method is a method of treating a muscle disease; and the muscle disease is selected from the group consisting of myopathies, muscular dystrophies, motor neuron diseases, and cardiomyopathies.

3. The method of claim 2, wherein the muscle disease is a muscular dystrophy; and said muscular dystrophy is selected from the group consisting of dystrophinopathies, Duchenne muscular dystrophy, Becker muscular dystrophy, myotonic dystrophies, Eimery-Dreifuss muscular dystrophy, limb-girdle disease, facioscapulohumeral muscular dystrophy, oculopharyngeal muscular dystrophy, distal muscular dystrophy, congenital muscular dystrophy, juvenile macular dystrophy, centronuclear myopathy, central core myopathy, and inclusion body myositis.

4. The method of claim 2, wherein the muscle disease is a motor neuron disease; and the motor neuron disease is selected from the group consisting of amyotrophic lateral sclerosis, spinal muscular atrophy, and spinal bulbar muscular atrophy.

5. The method of claim 2, wherein the muscle disease is a cardiomyopathy; and the cardiomyopathy is selected from the group consisting of hypertrophic cardiomyopathy and dilated cardiomyopathy.

6. The method of claim 1, wherein the isoprenoid antibiotic is a compound of formula 1:

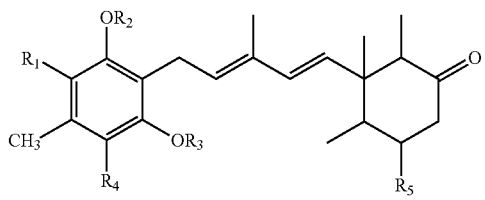

wherein $R_1$ is selected form the group consisting of CHO, $C_2H_2COCH_3$, $C(OCH_3)_2$, $C(OCH_2CH_3)_2$, $C(O(CH_2)_3 CH_3)_2$, $CO_2H$ and

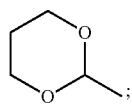

$R_2$ is selected form the group consisting of H, $CH_3$, and $CH_3CO$;

$R_3$ is selected form the group consisting of H, $CH_3$, $CH_2CH_3$, allyl, butyl, nicotinyl, benzoyl, isonicotinoyl, $CH_2COOH$, $(CH_2)_2COOH$, $(CH_2)_3COOH$, $(CH_2)_3 COOH$, $CH_2COO$ $CH_3$, $OCH_2COOC_2H_5$, $OCH_2COOCH_3$, $OCH_2COOH$, $OCHCH_3COOC_2H_5$, $OCHCH_3COOC_4H_9$, $OCHCH_2CH_3COOC_2H_5$, $O(CH_2)_3COOC_2H_5$, $OCHCH_3COOH$, $O(CH_2)_3 COOH$, $OCOC_6H_4OCH_3$, $OCOC_6H_4COOCH_3$, $OCON (C_2H_5)$, $OCOCH_2OC_6H_4Cl$, $OCH_3$, $O(CH_2)_3CH_3$, $OCH_2CH_3$, $OCH_2CHCH_2$, $CH_3CO$,

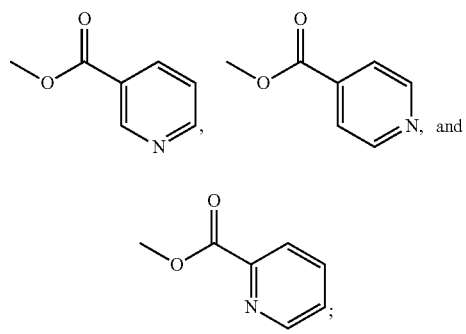

$R_4$ is selected form the group consisting of Cl, Br, and H; and $R_5$ is selected form the group consisting of H, O, and OAc.

7. The method of claim 1, wherein the isoprenoid antibiotic is a compound of formula 2:

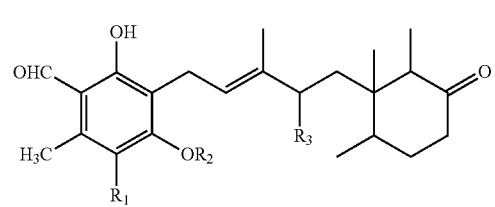

wherein $R_1$ is selected form the group consisting of H or Cl;

$R_2$ is selected form the group consisting of H, $CH_3$, and $CH_3CO$; and $R_3$ is selected form the group consisting of H, OH, OAc, $OCO(CH_3)_2$, and $OCOCH_2C(CH_3)_2$.

8. The method of claim 1, wherein the isoprenoid antibiotic is ascochlorin.

9. A method of upregulating hnRNP L or a hnRNP L target to treat a muscle disease or improve muscle function, comprising the step of administering to a mammal in need thereof a therapeutically effective amount of an isoprenoid antibiotic.

10. The method of claim 9, wherein the isoprenoid antibiotic is a compound of formula 1:

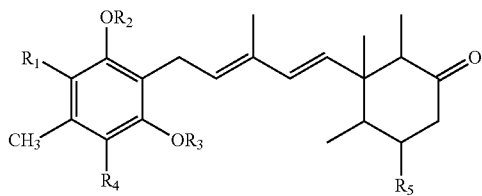

wherein

R₁ is selected form the group consisting of CHO, C₂H₂COCH₃, C(OCH₃)₂, C(OCH₂CH₃)₂, C(O(CH₂)₃CH₃)₂, CO₂H and

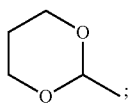;

R₂ is selected form the group consisting of H, CH₃, and CH₃CO;

R₃ is selected form the group consisting of H, CH₃, CH₂CH₃, allyl, butyl, nicotinyl, benzoyl, isonicotinoyl, CH₂COOH, (CH₂)₂COOH, (CH₂)₃COOH, (CH₂)₃COOH, CH₂COO CH₃, OCH₂COOC₂H₅, OCH₂COOCH₃, OCH₂COOH, OCHCH₃COOC₂H₅, OCHCH₃COOC₄H₉, OCHCH₂CH₃COOC₂H₅, O(CH₂)₃COOC₂H₅, OCHCH₃COOH, O(CH₂)₃COOH, OCOC₆H₄OCH₃, OCOC₆H₄COOCH₃, OCON(C₂H₅), OCOCH₂OC₆H₄Cl, OCH₃, O(CH₂)₃CH₃, OCH₂CH₃, OCH₂CHCH₂, CH₃CO,

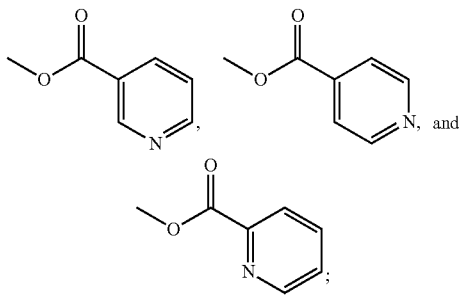

R₄ is selected form the group consisting of Cl, Br, and H; and

R₅ is selected form the group consisting of H, O, and OAc.

11. The method of claim 9, wherein the isoprenoid antibiotic is a compound of formula 2:

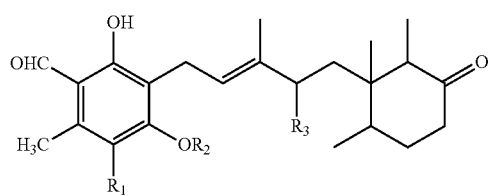

wherein

R₁ is selected form the group consisting of H or Cl;

R₂ is selected form the group consisting of H, CH₃, and CH₃CO; and

R₃ is selected form the group consisting of H, OH, OAc, OCO(CH₃)₂, and OCOCH₂C(CH₃)₂.

12. The method of claim 9, wherein the isoprenoid antibiotic is ascochlorin.

13. The method of claim 9, wherein the method is a method of upregulating a hnRNP L target; and the hnRNP L target is selected from the group consisting of ABI1, ACSS2, AGAP3, AGXT2L2, APP, ATP2B1, ATP2B4, BIN1, BPTF, C12orf41, C14orf133, DMD, DTNA, EIF 2C2, EPB41L2, FMNL2, GARNL1, GLUT-1, IT SN2, KIAA1217, LRRF IP1, MAPT, MAX, MEF2A, NCAM1, PALLD, PDLIM7, PPP2R5C, PTPN3, RPGR, RRN3, SAD1, SAMD4A, SEMA6D, SLC25A3, SLC39A9, SMTN, SORBS1, STXBP5, SVIL, TPM1, TPM3, TRIM66, TTN, VEGF, VPS29, XPNPEP1 and ZMYND8.

14. The method of claim 1, wherein the muscle disease is sarcopenia.

15. The method of claim 1, wherein the mammal is a human.

16. The method of claim 2, wherein the mammal is a human.

17. The method of claim 6, wherein the mammal is a human.

18. The method of claim 7, wherein the mammal is a human.

19. The method of claim 8, wherein the mammal is a human.

20. The method of claim 14, wherein the mammal is a human.

* * * * *